(12) United States Patent
Sah

(10) Patent No.: US 8,202,524 B2
(45) Date of Patent: Jun. 19, 2012

(54) METHOD FOR PRODUCING MICROSPHERES LOADED WITH DRUGS AND MICROSPHERES LOADED WITH DRUGS PRODUCED THEREBY

(75) Inventor: Hong Kee Sah, Seoul (KR)

(73) Assignees: SK Chemicals Co., Ltd., Suwon, Gyeonggi-do (KR); EWHA University-Industry Collaboration Foundation, Seodaemun-Gu, Seoul (KR)

( * ) Notice: Subject to any disclaimer, the term of this patent is extended or adjusted under 35 U.S.C. 154(b) by 395 days.

(21) Appl. No.: 12/310,398

(22) PCT Filed: Aug. 31, 2007

(86) PCT No.: PCT/KR2007/004200
§ 371 (c)(1),
(2), (4) Date: Feb. 24, 2009

(87) PCT Pub. No.: WO2008/026894
PCT Pub. Date: Mar. 6, 2008

(65) Prior Publication Data
US 2009/0318569 A1 Dec. 24, 2009

(30) Foreign Application Priority Data

Aug. 31, 2006 (KR) .................. 10-2006-0083648

(51) Int. Cl.
*A61K 9/00* (2006.01)
*A61K 47/30* (2006.01)
*A61K 47/00* (2006.01)
*A01N 25/00* (2006.01)

(52) U.S. Cl. ............ 424/400; 514/772.7; 514/772.3; 514/783; 514/788

(58) Field of Classification Search .............. None
See application file for complete search history.

(56) References Cited

U.S. PATENT DOCUMENTS

| | | |
|---|---|---|
| 3,691,090 A | 9/1972 | Kitajima et al. |
| 3,891,570 A | 6/1975 | Fukushima et al. |
| 4,389,840 A | 6/1983 | Briner et al. |
| 4,530,840 A | 7/1985 | Tice et al. |
| 5,271,945 A | 12/1993 | Yoshioka et al. |
| 5,298,474 A * | 3/1994 | Luciani et al. .............. 502/115 |
| 5,985,177 A * | 11/1999 | Yoshida et al. .............. 516/113 |
| 5,985,309 A | 11/1999 | Edwards et al. |
| 6,149,944 A | 11/2000 | Jeong et al. |
| 6,270,700 B1 | 8/2001 | Ignatious |
| 6,368,632 B1 | 4/2002 | Mesens et al. |
| 6,471,996 B1 | 10/2002 | Sokoll et al. |
| 6,544,559 B2 | 4/2003 | Mesens et al. |
| 6,572,894 B2 | 6/2003 | Rossling et al. |
| 6,884,435 B1 | 4/2005 | O'Hagan et al. |
| 2004/0156911 A1 * | 8/2004 | Chattopadhyay et al. .... 424/489 |

FOREIGN PATENT DOCUMENTS

| | | |
|---|---|---|
| KR | 2002-0000698 | 1/2002 |
| KR | 2004-0042152 | 5/2004 |
| WO | WO 93/07861 | 4/1993 |
| WO | WO 97/41837 | 11/1997 |
| WO | WO 2005042219 A1 * | 5/2005 |

* cited by examiner

*Primary Examiner* — Michael G Hartley
*Assistant Examiner* — Lance Rider
(74) *Attorney, Agent, or Firm* — Buchanan Ingersoll & Rooney PC

(57) ABSTRACT

The present invention relates to a method for producing polymeric microspheres loaded with drugs and polymeric microspheres loaded with drugs produced thereby, specifically a method for producing polymeric microspheres loaded with drugs, the method comprising the steps of a) adding a dispersion phase containing a high molecular compound, a drug, and a water-insoluble organic solvent to a dispersion solvent to produce an O/W (oil-in-water) type or O/O (oil-in-oil) type emulsion, or adding a W/O (water-in-oil) type emulsion, which is prepared by emulsifying an aqueous solution, in which a drug is dissolved, in a water-insoluble organic solvent, in which the high molecular compound is dissolved, to the dispersion solvent to produce a W/O/W (water-in-oil-in-water) type emulsion; and b) adding an ammonia solution to the emulsion produced in step a) to convert the water-insoluble organic solvent into water-soluble solvents, and polymeric microspheres loaded with drugs produced thereby. According to the present invention, the desired polymeric microspheres loaded with drugs can be simply produced with a small amount of water in a short period of time.

12 Claims, 12 Drawing Sheets

US 8,202,524 B2

METHOD FOR PRODUCING MICROSPHERES LOADED WITH DRUGS AND MICROSPHERES LOADED WITH DRUGS PRODUCED THEREBY

TECHNICAL FIELD

The present invention relates to a method for producing polymeric microspheres loaded with drugs and polymeric microspheres loaded with drugs produced thereby, in particular, a method for producing polymeric microspheres loaded with drugs comprising the steps of producing an emulsion by adding a dispersion phase containing a high molecular compound, a drug, and a water-insoluble organic solvent to a dispersion solvent and adding an ammonia solution to the produced emulsion to convert the water-insoluble organic solvent into water-soluble solvents, and polymeric microspheres loaded with drugs produced by the method.

BACKGROUND ART

Conventional injectable formulations such as solution, suspension, and emulsion are quickly removed from the body after intramuscular or subcutaneous administration, and therefore frequent administration is essentially needed for treatment of chronic diseases. Microencapsulation has been developed to solve the problem, and referred to a production process for encapsulating drugs in microspheres (hereinafter, the term microsphere will include nanospheres) consisting of high molecular compounds. Microspheres are usually in a size of μm unit, and can be administered to a human or animal by intramuscular or subcutaneous injection. Further, microspheres can be produced to have a variety of drug release rates, so that the period of drug delivery can be controlled. Therefore, even if a therapeutic drug is administered only once, its effective concentration can be maintained over a long period of time, and the total administration amount of therapeutic drug can be minimized to improve the drug compliance in patients. Accordingly, world famous pharmaceutical companies are very interested in the production of polymeric microsphere loaded with drugs.

In the production of polymeric microspheres by microencapsulation, poly-d,l-lactide-co-glycolide (PLGA) has been most widely used as a high molecular compound. PLGA is a biocompatible high molecular compound that is hydrolyzed in vivo to be converted into nontoxic lactic acid and glycolic acid. Therefore, pharmaceutical industries have made extensive studies on the development of drug formulation using PLGA, and examples of current available microsphere product produced by using PLGA include Risperdal® Consta®, Sandostatin LAR®, Vivitrol®, and Lupron Depot®. Each of them is injected to a patient once to control the release of risperidone, octreotide acetate, naltrexone, and leuprolide acetate from 2 weeks to 4 months.

Such polymeric microspheres loaded with drugs can be conventionally produced by a solvent evaporation method or a solvent extraction method using an organic solvent such as methylene chloride and ethyl acetate.

First, the solvent evaporation method will be briefly described (see U.S. Pat. Nos. 6,471,996, 5,985,309, and 5,271,945). A drug is dispersed or dissolved in an organic solvent in which a high molecular compound is dissolved, and then emulsified in a dispersion medium such as water to produce an oil-in-water (O/W) emulsion. Then the organic solvent in the emulsion is diffused into a dispersion medium and evaporated across the air/water interface to form the polymeric microspheres loaded with drugs. At this time, in order to accelerate the diffusion of organic solvent into the dispersion medium, the organic solvent extraction method using reduced pressure, increased temperature, and an excessive amount of water is used. A dispersion organic solvent that is generally used to dissolve the high molecular PLGA is methylene chloride. Methylene chloride can dissolve well a PLGA copolymer with various molecular weights and lactide:glycolide ratios and can not mix well with water due to the low water solubility of 1.32% by weight. Thus, methylene chloride is a suitable solvent for the production of oil-in-water emulsion. Further, due to the low boiling point of 39.8° C., small amounts of methylene chloride molecules that diffused from emulsion liquid droplets into water are evaporated across the water/air interface. Such process is continuously repeated to remove methylene chloride from emulsion droplets, thereby forming microspheres. Finally, the residual methylene chloride present in microspheres is easily dried and removed due to its low boiling point. Based on the solvent evaporation method, a diagram showing the conversion of the emulsion droplets into microspheres is shown in FIG. 1. As shown in FIG. 1, a dispersion phase consisting of PLGA/drug/methylene chloride exists in the outer phase, such as water, as a form of oil-in-water emulsion (methylene chloride dissolved in water is represented as Δ) (A), and if the diffusion of methylene chloride in water and its evaporation are repeated, the emulsion droplets are converted into microparticles as shown in (B).

Likewise, even though methylene chloride is the most optimal solvent used for the production of emulsion in that it is very volatile, not mixed well with water, and has a lower boiling point than water, methylene chloride has the following problems: (a) it is a carcinogen proved by experiments; (b) it destroys the ozone layer in the atmosphere to generate a toxic environment, causing an increase in human skin cancer; (c) it is one of the 38 toxic and hazardous substances announced by the Agency for Toxic Substances and Disease Registry within the US Department of Health and Human Services; (d) a lot of time is required to completely remove methylene chloride in the emulsion droplets, since it has a low water solubility of about 1.32% by weight and only small amounts of methylene chloride are dissolved in water and evaporates. For example, in U.S. Pat. No. 6,884,435, the emulsion is stirred overnight to remove methylene chloride from the emulsion, and conditions such as increased temperature or reduced pressure in a reactor are introduced to shorten the production time of microspheres (see U.S. Pat. Nos. 3,691,090, 3,891,570, 6,270,700, and 6,572,894).

On the other hand, the solvent extraction method used to produce polymeric microspheres loaded with drugs is a method for effectively extracting the organic solvent in the emulsion droplets by using a large amount of solubilizing solvent. When the organic solvent is extracted from the emulsion droplets, the dissolved high molecular compounds are hardened to convert the emulsion droplets into microspheres. The solubilizing solvent that is generally used is water, and the degree of water solubility of the organic solvent greatly affects the amount of water needed. For example, methylene chloride has water solubility of 1.32% by weight, whereby a very large amount of water is needed for extracting methylene chloride in the emulsion. However, a large amount of wastewater containing methylene chloride is produced, in which the treatment of the wastewater becomes a problematic issue. Therefore, in the solvent extraction method, ethyl acetate, which has higher water solubility than methylene chloride, is mainly used. Since ethyl acetate has the water solubility of 8.7% by weight, it can be extracted by using a relatively small amount of water, as compared to methylene chloride, and it is advantageously a nonhalogenated organic solvent. However, its boiling point is 77° C. and much higher than 39.8° C., which is that of methylene chloride. Thus, ethyl acetate has a drawback that the residual solvent is hard to remove when dried. Furthermore, a PLGA polymer with a specific molecular weight and lactide:glycolide ratio has a characteristic of not dissolving easily in ethyl acetate.

Therefore, technologies simultaneously employing the solvent evaporation method and solvent extraction method are disclosed in U.S. Pat. Nos. 4,389,840, 4,530,840, 6,544,559, 6,368,632, and 6,572,894. That is, in the methods, the emulsion is produced, and then the organic solvent is partially removed by the evaporation process, and the residual organic solvent is removed by the solvent extraction method. For example, U.S. Pat. No. 4,389,840 discloses a method for producing microspheres, in which a drug and a PLGA polymer are dissolved in methylene chloride and then emulsified in water to produce oil in water-type emulsion, then 40 to 60% by weight of methylene chloride is removed by the evaporation process, and the residual methylene chloride is extracted using a large amount of water to produce microspheres.

However, since all of the organic solvents used in the known methods do not have sufficient high water solubility, excessively large amounts of water (over 10 times more than water solubility of organic solvent) should be used. Thus, a large-volume reactor is needed, and a large amount of wastewater containing organic solvent is produced, as a result, the cost for wastewater treatment is increased. Further, there is a problem that the residual organic solvent present in the microspheres is not effectively removed.

Accordingly, the present inventors have studied to solve the problems and a method for simply producing polymeric microspheres loaded with drugs. We have found that the polymeric microspheres loaded with drugs can be simply produced by dissolving a polymeric compound and a drug in a water-insoluble organic solvent to produce an emulsion, and converting into a water-soluble solvent through ammonolysis to harden emulsion droplets into microspheres, thereby completing the present invention.

DISCLOSURE OF THE INVENTION

Technical Problem

Therefore, it is an object of the present invention to provide a method for producing polymeric microspheres loaded with drugs, in which a known solvent evaporation or solvent extraction process is not needed, and polymeric microspheres loaded with drugs produced thereby.

Technical Solution

In order to achieve the object, the present invention provides a method for producing polymeric microspheres loaded with drugs, the method comprising the steps of: a) adding a dispersion phase containing a high molecular compound, a drug, and a water-insoluble organic solvent to a dispersion solvent to produce an O/W (oil-in-water) type or O/O (oil-in-oil) type emulsion, or adding a W/O (water-in-oil) type emulsion, which is prepared by emulsifying an aqueous solution, in which a drug is dissolved, in a water-insoluble organic solvent, in which the high molecular compound is dissolved, to the dispersion solvent to produce a W/O/W (water-in-oil-in-water) type emulsion; and b) adding an ammonia solution to the emulsion produced in step a) to convert the water-insoluble organic solvent into water-soluble solvents.

Further, the present invention provides polymeric microspheres loaded with drugs produced by the method.

Hereinafter, the present invention will be described in more detail.

The production method according to the present invention is characterized in that the water-insoluble organic solvent present in the emulsion is converted into the water-soluble solvents through ammonolysis by the addition of an ammonia solution to the emulsion, so as to harden emulsion droplets into microspheres, thereby obtaining the desired polymeric microsphere loaded with drugs.

Each step of the method for producing polymeric microspheres according to the present invention will be described in detail as follows.

Step a): Step of Producing Emulsion

A dispersion phase containing a high molecular compound, a drug, and a water-insoluble organic solvent is added to a dispersion solvent to produce an O/W (oil-in-water) type or O/O (oil-in-oil) type emulsion, or an aqueous solution, in which the drug is dissolved, is emulsified in the water-insoluble organic solvent, in which the high molecular compound is dissolved, so as to produce a W/O (water-in-oil) type emulsion, and then added to the dispersion solvent to produce a W/O/W (water-in-oil-in-water) type emulsion.

The dispersion solvent used in the present invention includes an aqueous dispersion solvent or nonaqueous dispersion solvent containing an emulsifier, and the aqueous dispersion solvent is used during the preparation of an O/W type and W/O/W type emulsion, the nonaqueous dispersion solvent is used during the preparation of an O/O type emulsion. As the aqueous dispersion solvent, an aqueous solution containing a hydrophilic emulsifier such as polyvinyl alcohol or Tween series, or a co-solvent thereof can be used. As the nonaqueous dispersion solvent, silicone oil, vegetable oil, toluene, or xylene containing a hydrophobic emulsifier such as Span series can be used. The emulsifier in the dispersion solvent may be contained in a concentration of 0.05 to 15% (w/v).

In the present invention, any water-insoluble organic solvent can be used, as long as it is not mixed with water but decomposed by the reaction with ammonia to be converted into water-soluble solvents. Specifically, it is preferable that the water-insoluble organic solvent has any one backbone selected from the group consisting of carboxylic esters, carboxylic amides, anhydrides, phosphoric esters, and phosphoric anhydrides. More specifically, it is preferable that the water-insoluble organic solvent is selected from the group consisting of methyl dichloroacetate, methyl chloroacetate, ethyl chloroacetate, ethyl dichloroacetate, methyl fluoroacetate, methyl difluoroacetate, ethyl fluoroacetate, ethyl difluoroacetate, ethyl acetate, methyl acetate, methyl formate, ethyl formate, isopropyl formate, and propyl formate.

The water-insoluble organic solvents have not been generally used in the known method for producing microspheres due to their high boiling point. However, in the method for producing polymeric microspheres of the present invention, the water-insoluble organic solvents are reacted with ammonia to be converted into water-soluble solvents, thereby being preferably used in the present invention. Specifically, since methyl dichloroacetate and methyl chloroacetate used in Examples of the present invention have much higher boiling points (142.9° C., 129.5° C.) than methylene chloride and ethyl acetate that are usually used in the known solvent evaporation or solvent extraction method, they can not be used as an organic solvent in the known methods for producing microspheres. In the present invention, when methyl dichloroacetate or methyl chloroacetate is reacted with ammonia, it is converted into dichloroacetamide and methanol, or chloroacetamide and methanol that are completely dissolved in water within a very short time, thereby being preferably used. If necessary, a co-solvent that is a mixture of methyl dichloroacetate or methyl chloroacetate and at least one of the other organic solvents is used, whereby the solubility of a drug to be encapsulated in microspheres can be controlled or a rate of hardening emulsion droplets can be controlled, as desired.

Examples of the high molecular compound used in the present invention include polylactic acid, polylactide, polylactic-co-glycolic acid, polylactide-co-glycolide (PLGA), polyphosphazene, polyiminocarbonate, polyphosphoester, polyanhydride, polyorthoester, a copolymer of lactic acid and caprolactone, polycaprolactone, polyhydroxyvalerate, polyhydroxybutyrate, polyamino acid, a copolymer of lactic acid and amino acid, and a mixture thereof, preferably polylactide-co-glycolide (PLGA).

The drug used in the present invention includes all of hydrophilic drugs and hydrophobic drugs. Examples of the drug include progesterone, haloperidol, thiothixene, olanzapine, clozapine, bromperidol, pimozide, risperidone, ziprasidone, diazepam, ethyl loflazepate, alprazolam, nemonapride, fluoxetine, sertraline, venlafaxine, donepezil, tacrine, galantamine, rivastigmine, selegiline, ropinirole, pergolide, trihexyphenidyl, bromocriptine, benztropine, colchicine, nordazepam, etizolam, bromazepam, clotiazepam, mexazolum, buspirone, goserelin acetate, somatotropin, leuprolide acetate, octreotide, cetrorelix, sandostatin acetate, gonadotropin, fluconazole, itraconazole, mizoribine, cyclosporin, tacrolimus, naloxone, naltrexone, cladribine, chlorambucil, tretinoin, carmustine, anagrelide, doxorubicin, anastrozole, idarubicin, cisplatin, dactinomycin, docetaxel, paclitaxel, raltitrexed, epirubicin, letrozole, mefloquine, promaquine, oxybutynin, tolterodine, allylestrenol, lovastatin, simvastatin, pravastatin, atorvastatin, alendronate, salcatonin, raloxifene, oxadrolone, conjugated estrogen, estradiol, estradiol valerate, estradiol benzoate, ethinyl estradiol, etonogestrel, levonorgestrel, tibolone, and norethisterone, preferably risperidone or progesterone.

For the production of the hydrophobic drug, a high molecular compound and a hydrophobic drug are dissolved in a water-insoluble organic solvent, and then suspended in an aqueous dispersion solvent or nonaqueous dispersion solvent to produce an O/W type or O/O type emulsion. For the production of the hydrophilic drug, a hydrophilic drug is first dissolved in water, and then the solution is emulsified in an organic solvent, in which the high molecular compound is dissolved, so as to produce a primary W/O type emulsion. Then, the emulsion is suspended in an aqueous dispersion solvent to produce a secondary W/O/w type emulsion.

The high molecular compound can be used in an amount of 1 to 500 parts by weight, preferably 1 to 50 parts by weight, based on 1 part by weight of the drug, and the concentration of the high molecular compound contained in the emulsion may be 3 to 30% (w/v).

Further, the volume ratio of the dispersion phase or W/O (water-in-oil) type emulsion and the dispersion solvent may be in a range of 1:1 to 100, preferably 1:3 to 15. The volume ratio of the aqueous solution, in which the drug is dissolved, and the water-insoluble organic solvent, in which the high molecular compound is dissolved, may be in a range of 1:1 to 50, preferably 1:2 to 20.

Step b): Step of Converting Water-Insoluble Organic Solvent into Water-Soluble Solvent An ammonia solution is added to the O/W type, W/O/W type, or O/O type emulsion produced in step a), and the water-insoluble organic solvent is converted into solvents that are completely dissolved in water through ammonolysis. Then, the emulsion droplets are hardened into microspheres to produce the desired polymeric microspheres loaded with drugs. At this time, the interaction between particles of emulsion droplets is inhibited due to the rapid hardening of the emulsion droplets, thereby obtaining the desired microspheres without the cohesion of the droplets.

In one embodiment according to the present invention, a diagram showing the production process of a polymeric microsphere containing a drug (risperidone) is illustrated in FIG. 2. In FIG. 2, a dispersion phase consisting of PLGA/risperidone/methylene dichloroacetate is emulsified in an outer water phase (□) as liquid droplets (A), and then by ammonolysis, methylene dichloroacetate is converted into dichloroacetamide (▼) and methanol (▲) that are completely dissolved in water to produce the desired microsphere (B). The ammonia solution used in the present invention suitably contains higher molarity of ammonia than that of water-insoluble organic solvent.

In another embodiment according to the present invention, a diagram showing the production process of a polymeric microsphere containing a drug (progesterone) is illustrated in FIG. 7. In FIG. 7, a dispersion phase consisting of PLGA/progesterone/methyl chloroacetate is emulsified in an outer water phase as liquid droplets, and then by ammonolysis, methyl chloroacetate is converted into chloroacetamide and methanol that are completely mixed with water to produce the desired microsphere.

The polymeric microspheres produced by the method of the present invention has a mean diameter of 0.1 to 3500 µm, preferably 10 to 350 µm, and can contain drugs having a variety of weights, as desired.

As described above, according to the present invention polymeric microspheres loaded with drugs can be simply produced in a short period of time, in which the known solvent evaporation or solvent extraction process is not required, and a small amount of water is used to minimize the generation of wastewater.

Advantageous Effects

Accordingly, the desired polymeric microspheres loaded with drugs can be simply produced in a short period of time according to the present invention, in which the known solvent evaporation or solvent extraction process is not required, and a small amount of water is used to minimize the generation of wastewater.

BEST MODE FOR CARRYING OUT THE INVENTION

Hereinafter, the present invention will be described in more detail with reference to following Examples. However, these Examples are for illustrative purpose only, and the invention is not intended to be limited by these Examples.

Example 1

Ammonolysis Using Methyl Dichloroacetate

<1-1> Ammonolysis of Methyl Dichloroacetate

In order to confirm the conversion of a water-insoluble organic solvent into solvents that are completely mixed with water through ammonolysis, the present inventors performed the following experiments using methyl dichloroacetate as a water-insoluble organic solvent.

3 ml of methyl dichloroacetate was added to 40 ml of water containing 1% polyvinyl alcohol (88% hydrolyzed, molecular weight: 25,000), and stirred at 550 rpm to produce an emulsion. After stirring for 3 minutes, 3 ml of ammonia solution (about 30% concentration) was added to the emulsion. After 5 minutes, methyl dichloroacetate droplets dispersed in water completely disappeared, and the emulsion changed to be a one-phase solution. From the results, it was found that methyl dichloroacetate was converted into dichloroacetamide and methanol through ammonolysis, and completely mixed with water (for reference, the water solubility of dichloroacetamide is 71 g/l).

<1-2> Separation of Dichloroacetamide as Decomposition Product of Methyl Dichloroacetate An excessive amount of NaCl was added to a clear solution obtained in <1-1> to salt-out the decomposition product of methyl dichloroacetate, and then ethyl acetate was added thereto. The salted-out product was transferred to the ethyl acetate phase, and separated from an aqueous layer. Anhydrous $MgSO_4$ was added to remove water present in ethyl acetate, filtered, and then ethyl acetate was evaporated and removed using a rotary evaporator (Eyela Model N-1000). In order to remove ethyl acetate in the residual, the residual was washed with $CHCl_3$ once, and then dried under vacuum to obtain a white powder.

<1-3> Isolation of Dichloroacetamide by NMR and MS Experiments

Figure 1:
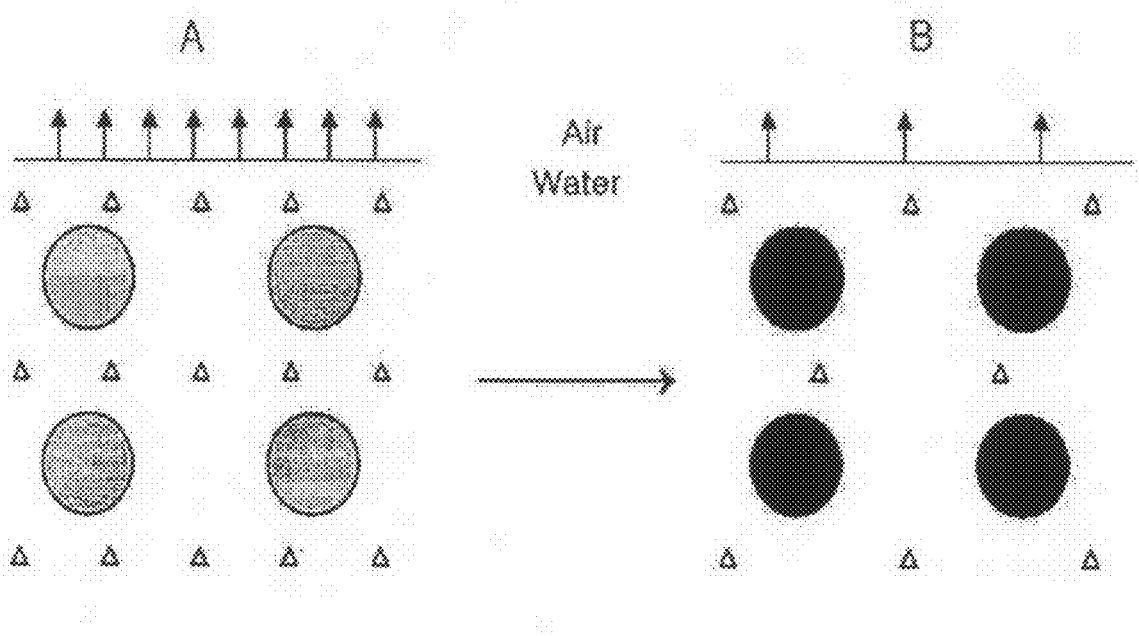
FIG. 1 is a diagram showing the conversion of emulsion droplets into microspheres based on a known solvent evaporation method.
Figure 2:
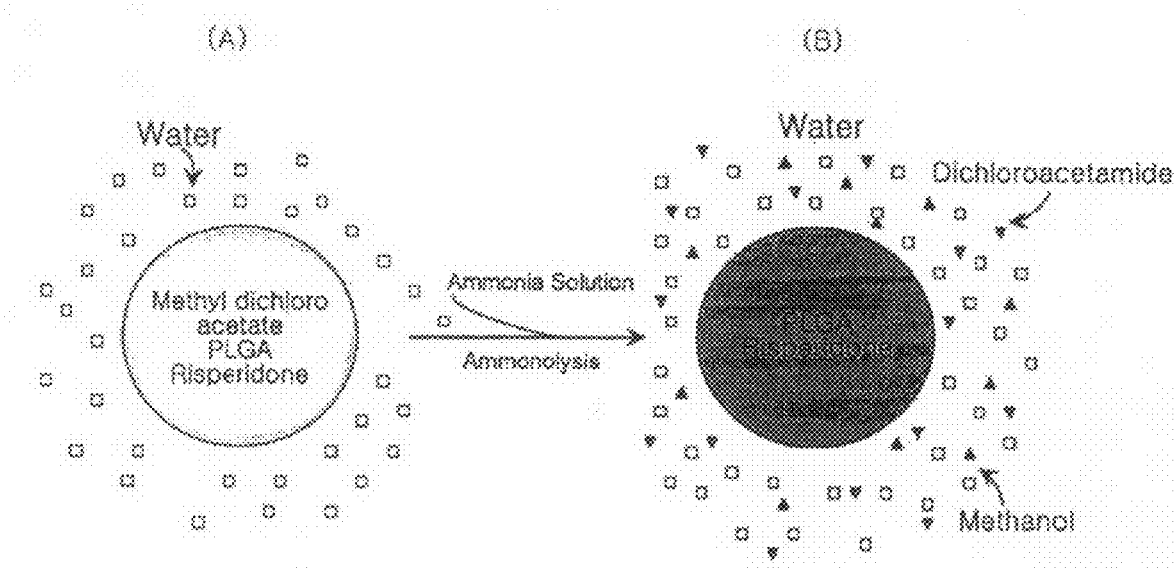
FIG. 2 is a diagram showing the production process of a polymeric microsphere containing a drug (risperidone) in one embodiment according to the present invention.
Figure 3:
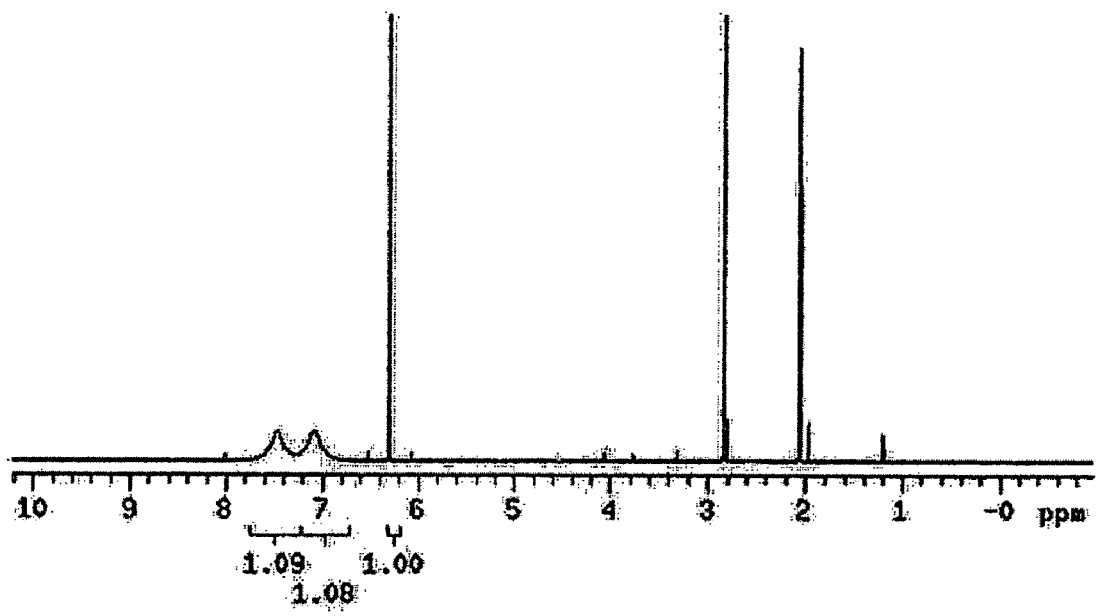
FIGS. 3 and 4 are $^1$H-NMR and Electrospray Ionization Mass Spectrometry (ESI-MS) of dichloroacetamide that is produced in the process of performing one embodiment according to the present invention, respectively.
Figure 4:
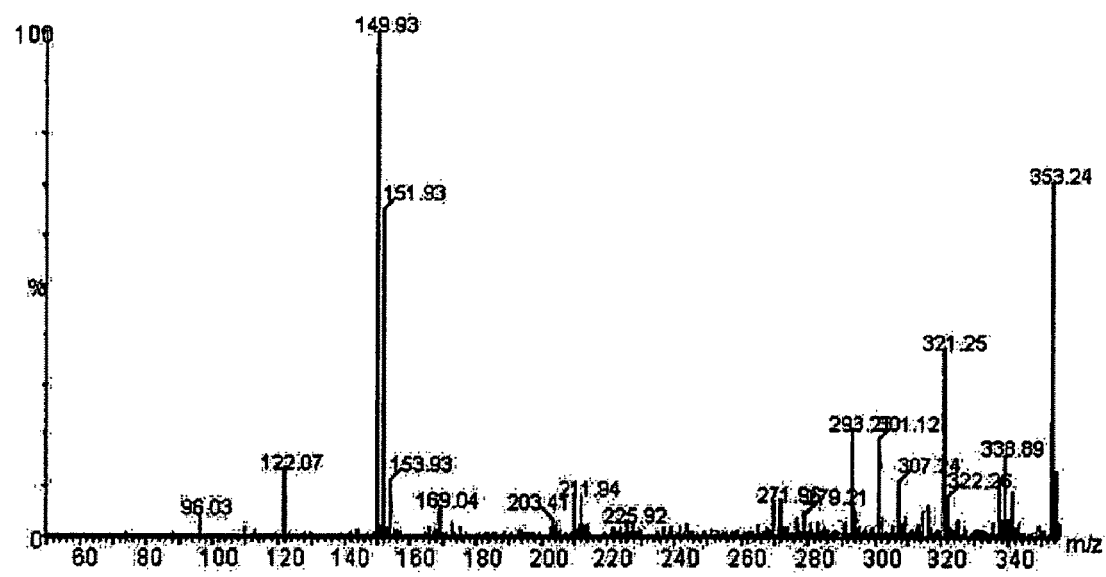

NMR and MS experiments of the white powder obtained in <1-2> were performed as follows: the white powder was dissolved in acetone-d6, and then $^1$H-NMR spectrum was observed by using an NMR spectrophotometer, the result is shown in FIG. 3. At this time, the $^1$H chemical shift was measured with respect to tetramethylsilane. As shown in FIG. 3, two amide proton signals were observed at δH 7.46 and 7.08. Further, a proton signal linked to carbon having two chloride groups was observed at δH 6.30. Electrospray Ionization Mass Spectrometry (ESI-MS) was observed by using a Q-tof™ 2 mass spectrometer, and the result is shown in FIG. 4. As shown in FIG. 4, a [M+Na$^+$] peak was observed at m/z 149.93, a [M+2+Na$^+$] peak was observed at m/z 151.93, and a [M+4+Na$^+$] peak was observed at m/z 153.93. The measured value of the present experiment completely corresponded to the theoretical value, considering that the intensity of [M+Na$^+$], [M+2+Na$^+$], and [M+4+Na$^+$] peaks of a compound having two chloride groups are 100, 65.3, and 10.6%. From the results of the $^1$H-NMR and ESI-MS experiments, methyl dichloroacetate was found to be converted into dichloroacetamide through ammonolysis.

From the results, it was found that methyl dichloroacetate as a water-insoluble organic solvent was converted into dichloroacetamide and methanol that are water-soluble organic solvents through ammonolysis.

Example 2

Ammonolysis Using Methyl Chloroacetate

<2-1> Ammonolysis of Methyl Chloroacetate

In order to confirm the conversion of a water-insoluble organic solvent into solvents that are completely mixed with water through ammonolysis, the present inventors performed the following experiments using methyl chloroacetate (water solubility is 46 g/l at 25° C.) as a water-insoluble organic solvent.

4 ml of methyl chloroacetate was added to 40 ml of water, and stirred using a hot plate stirrer (400 HPS/VWR Scientific) for 3 minutes to produce an emulsion. Then 4 ml of ammonia solution (about 30% concentration) was added to the emulsion. After 10 minutes, methyl chloroacetate droplets dispersed in water completely disappeared, and the emulsion changed to be a one-phase solution.

Figure 5:
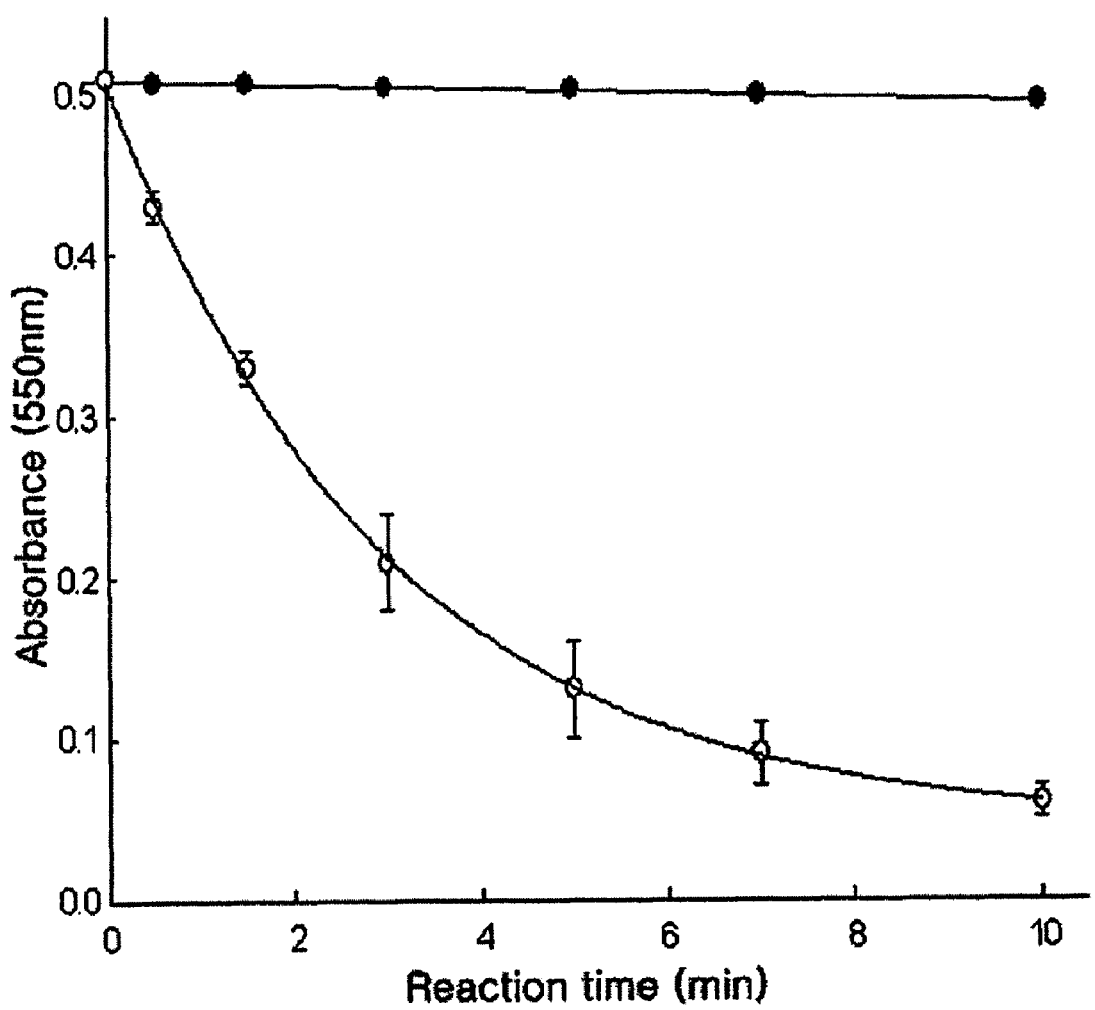
FIG. 5 is a curve showing the absorbance of an ammonia solution containing methyl chloroacetate produced in the presence of phenolphthalein during the process of performing one embodiment according to the present invention, in which the absorbance is measured depending on time, ● : in the absence of methyl chloroacetate ○ : in the presence of methyl chloroacetate.

Further, 100 ul of methanolic phenolphthalein solution was added to an aqueous solution, in which 4 ml of ammonia solution was added to 40 ml of water, and mixed with 4 ml of methyl chloroacetate. Then, 1 ml of the mixture was taken and its absorbance was measured depending on time at 550 nm using a U-3000 UV/Vis spectrometer (Shimadzu Corp. Kyoto, Japan), the result is shown in FIG. 5. As shown in FIG. 5, in the case of adding no methyl chloroacetate, there was no change in the absorbance. However, in the case of adding methyl chloroacetate, the absorbance sharply decreased.

From the results, it was found that methyl chloroacetate was converted into chloroacetamide and methanol through ammonolysis, and completely mixed with water.

<2-2> Separation of Chloroacetamide as Decomposition Product of Methyl Chloroacetate An excessive amount of NaCl was added to a clear solution obtained in <2-1>, and salted-out to precipitate chloroacetamide. Then 30 ml of ethyl acetate was added thereto three times. Chloroacetamide is transferred to the ethyl acetate phase, and separated from an aqueous layer. Anhydrous $MgSO_4$ was added to remove water present in ethyl acetate, filtered through celite, and then ethyl acetate was evaporated under reduced pressure to obtain a white powder.

<2-3> Isolation of Chloroacetamide by NMR and MS Experiments

Figure 6:
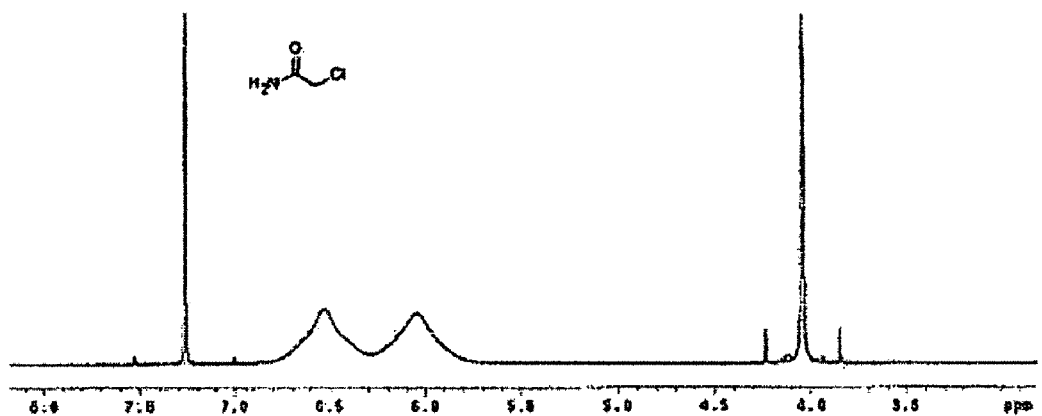
FIG. 6 is $^1$H-NMR (FIG. 6A) and Electrospray Ionization Mass Spectrometry (ESI-MS) (FIG. 6B) of chloroacetamide that is produced during the process of performing one embodiment according to the present invention.
Figure 6:
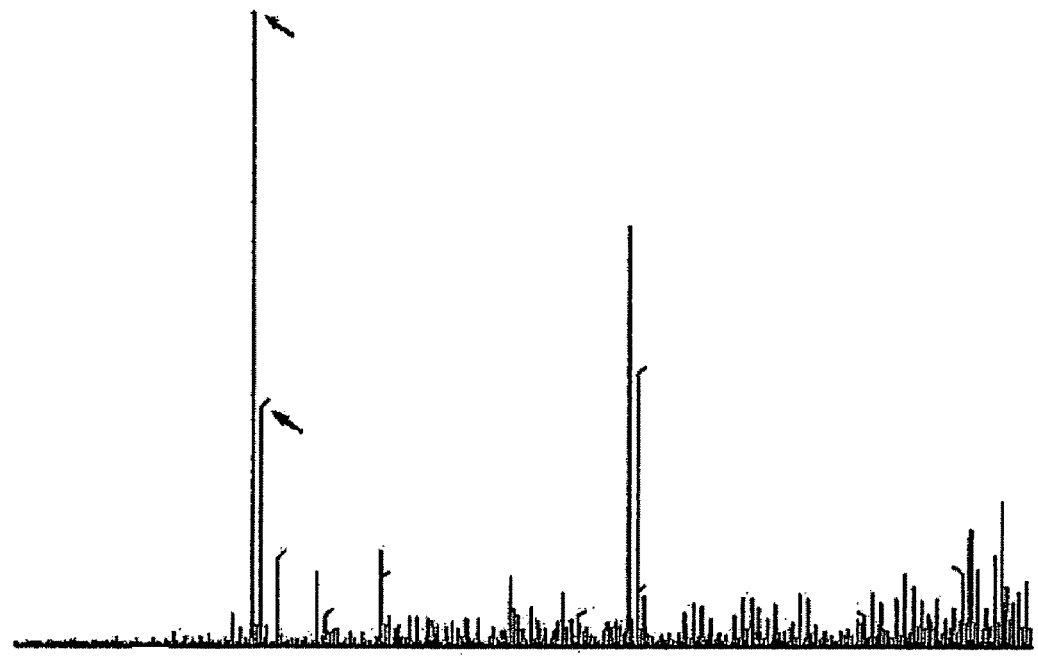

NMR and MS experiments of the white powder obtained in <2-2> were performed as follows; the white powder was dissolved in deuterated trichloromethane ($CDCl_3$), and then $^1H$-NMR spectrum was observed by using an NMR spectrophotometer, the result is shown in FIG. 6A. At this time, the $^1H$ chemical shift was measured with respect to tetramethylsilane. As shown in FIG. 6A, two amide proton signals were observed at δH 6.55 and 6.04. Further, a proton signal linked to carbon having a chloride group was observed at δH 4.05.

Further, Electrospray Ionization Mass Spectrometry (ESI-MS) was observed by using a Q-tof™ 2 mass spectrometer, and the result is shown in FIG. 6B. As shown in FIG. 6B, a $[M+Na^+]$ peak was observed at m/z 116.01, and a $[M+2+Na^+]$ peak was observed at m/z 118.01. The ratio of the two peaks was 3:1, which corresponds to the abundance of $^{37}Cl$.

Figure 7:
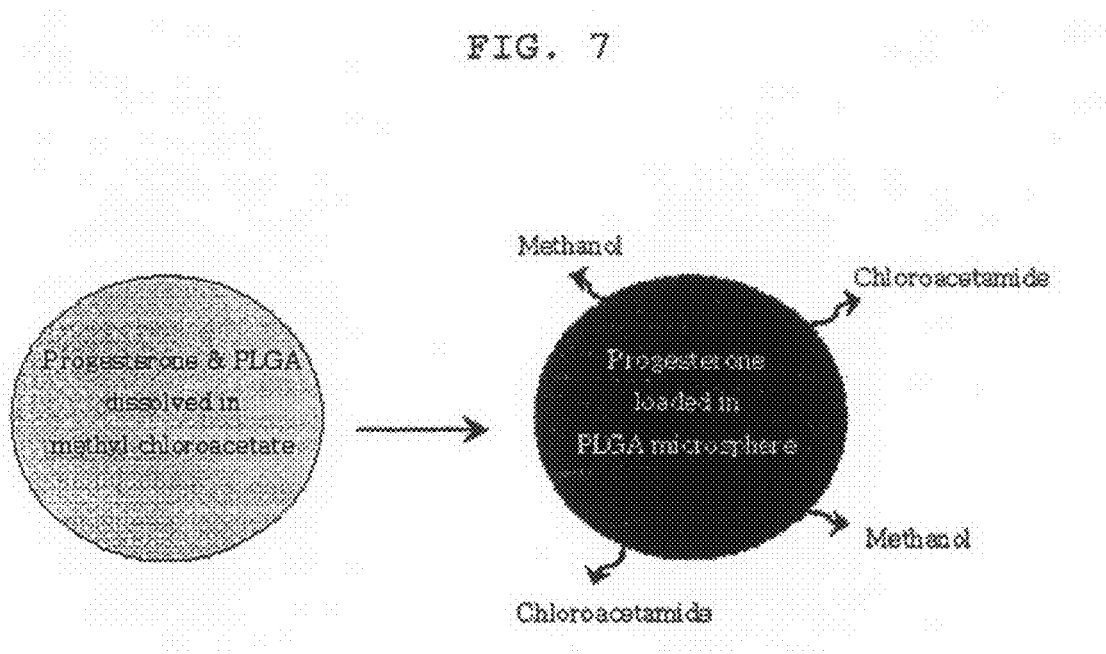
FIG. 7 is a diagram showing the production process of a microparticle through ammonolysis.

From the results of the $^1H$-NMR and ESI-MS experiments, methyl chloroacetate was found to be converted into chloroacetamide ($C_2H_4ClNO$) through ammonolysis. Specifically, it was found that methyl chloroacetate as a water-insoluble organic solvent was converted into chloroacetamide and methanol that are water-soluble organic solvents through ammonolysis (see FIG. 7).

Example 3

PLGA Microsphere Using Methyl Dichloroacetate

<3-1> Production of PLGA Microsphere Using Methyl Dichloroacetate

Poly-d,l-lactide-co-glycolide having the lactide:glycolide ratio of 75:25 (intrinsic viscosity in $CHCl_3$ is 0.67 dL/g; hereinbelow, represented by PLGA) was used as a high molecular compound for microsphere production. Risperidone (purchased from Changzhou United Chemical Co., Ltd, China) was used as a hydrophobic drug to be encapsulated in microspheres. PLGA (250 mg) was completely dissolved in 3 ml of methyl dichloroacetate, and then risperidone (125, 175, or 225 mg) was added thereto to be dissolved. A dispersion phase consisting of PLGA, risperidone, and methyl dichloroacetate was added to 40 ml of 1% aqueous solution of polyvinyl alcohol (molecular weight=25,000; 88% hydrolyzed), and emulsified. At this time, a magnetic stirrer was used to produce an emulsion, and the stirring speed of a magnetic bar was maintained at 550 rpm. After stirring for 3 minutes, 3 ml of ammonia solution (about 30% concentration) was added to the emulsion, and stirred for 15 minutes. The formed microsphere suspension was passed through a sieve having a size of 425 μm. Then, the microspheres were taken by filtration, and dispersed in 100 ml of 0.1% aqueous solution of polyvinyl alcohol. After 45 minutes, the microspheres was filtered and separated, and then re-dispersed in 100 ml of 0.1% aqueous solution of polyvinyl alcohol, and stirred for 2 hours. The microspheres taken by filtration were dried under vacuum overnight. After drying, the microspheres were found to have good fluidity, which indicates that the cohesion between microspheres was not strong during the drying process. Further, the yield of microspheres was found to be 76.4 to 86.4%, which indicates that the microspheres were effectively produced by the method of the present invention.

<3-2> Thermogravimetric Analysis

Figure 8:
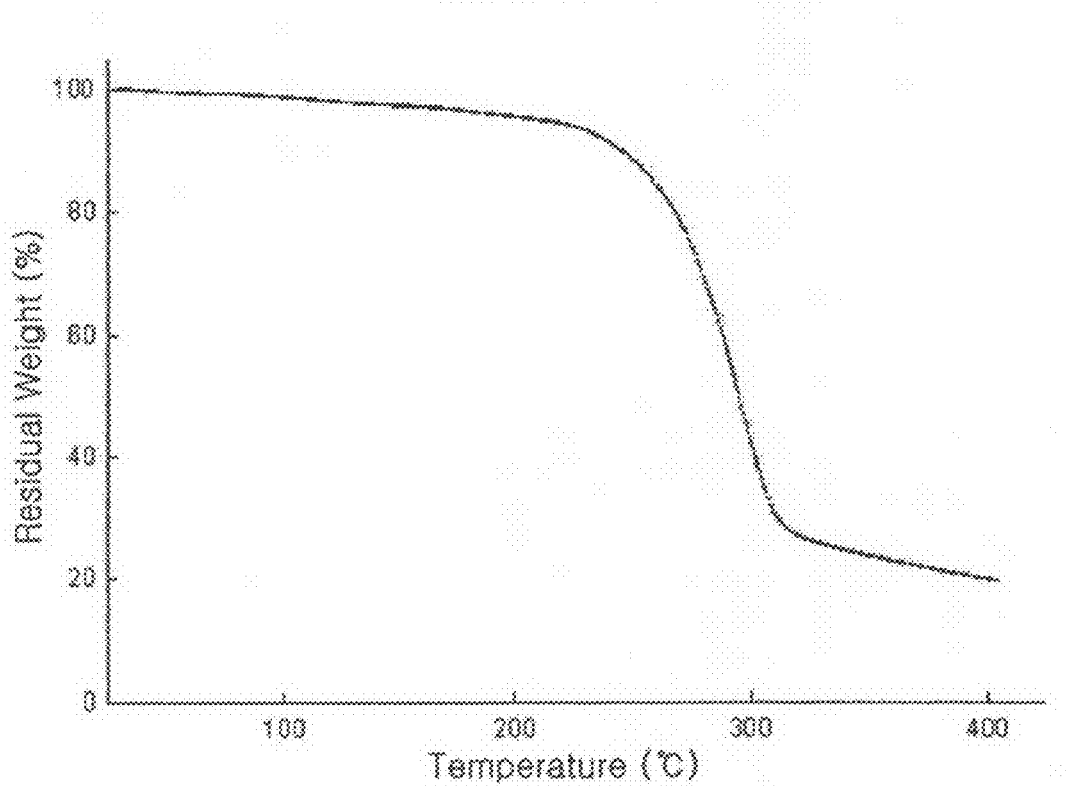
FIG. 8 is a thermogravimetric analysis curve of a polymeric microsphere containing a drug (risperidone) produced in one embodiment according to the present invention.

Thermogravimetric analysis of the microspheres that were produced by using 250 mg of PLGA and 125 mg of risperidone was performed by using a thermal-gravimetric analyzer, TGA 2050 (TA Instruments, US), and the results are shown in FIG. 8. In this connection, nitrogen gas was used, and the change in the microsphere weight was measured when the temperature was increased at a rate of 10° C. per minute. As shown in FIG. 8, there was no dramatic change in its weight at 142.9° C., which is the boiling point of methyl dichloroacetate. From the results, it was found that upon producing microspheres, methyl dichloroacetate was converted into water-soluble dichloroacetamide and methanol, and effectively removed from the emulsion droplets, whereby microspheres were formed.

<3-3> HPLC Analysis of Drug

A Shimadzu HPLC system was used for drug analysis. A symmetry C18 column (5 μm) having a length of 15 cm was used as an analysis column. A mixed solution of 10 mM ammonium acetate and methanol (volume ratio of 6:4) was used as a mobile phase, and the mobile phase flow rate was maintained at 1 ml/min. The drug flowing out of the HPLC column was measured at a UV wavelength of 260 nm. The drug concentration of the sample was determined from the standard calibration curve constructed with four different concentrations.

<3-4> Determination of Encapsulation Efficiency of Risperidone

Some of PLGA microspheres containing risperidone were precisely measured, and completely dissolved in 4 ml of tetrahydrofuran. 16 ml of methanol was added thereto, and filtered with a nylon filter having a pore size of 0.45 μm. The PLGA precipitate was removed therefrom, and the filtrate was prepared. Some of the filtrate (20 μl) was applied to HPLC, and the drug concentration was determined. According to the following Equations 1 to 3, a theoretical loading dose (%) and practical loading dose (%) of the drug were determined, and the percentage thereof was defined as the drug encapsulation efficiency (%).

$$\text{Theoretical loading dose \%} = 100 \times \frac{\text{Drug dose used (mg)}}{\text{PLGA dose used (mg)} + \text{Drug dose used (mg)}} \quad \text{[Equation 1]}$$

$$\text{Practical loading dose \%} = \quad \text{[Equation 2]}$$
$$100 \times \frac{\text{Drug dose present in microsphere (mg)}}{\text{Microsphere dose used for measurement of loading dose (mg)}}$$

$$\text{Encapsulation efficiency \%} = \quad \text{[Equation 3]}$$
$$100 \times \frac{\text{Practical loading dose (\%)}}{\text{Theoretical loading dose (\%)}}$$

In the case of using 250 mg of PLGA and 125 mg of risperidone, the encapsulation efficiency was 97.0±2.1%. In the case where the amount of PLGA was fixed and the amount of risperidone was increased by 175 and 225 mg, each of encapsulation efficiency was 94.5±2.0 and 92.7±3.2%. From the results, it was found that in the case of producing microspheres according to the method of the present invention, risperidone can be mostly encapsulated in the PLGA microspheres.

<3-5> Observation of Microsphere Shape

Figure 9:
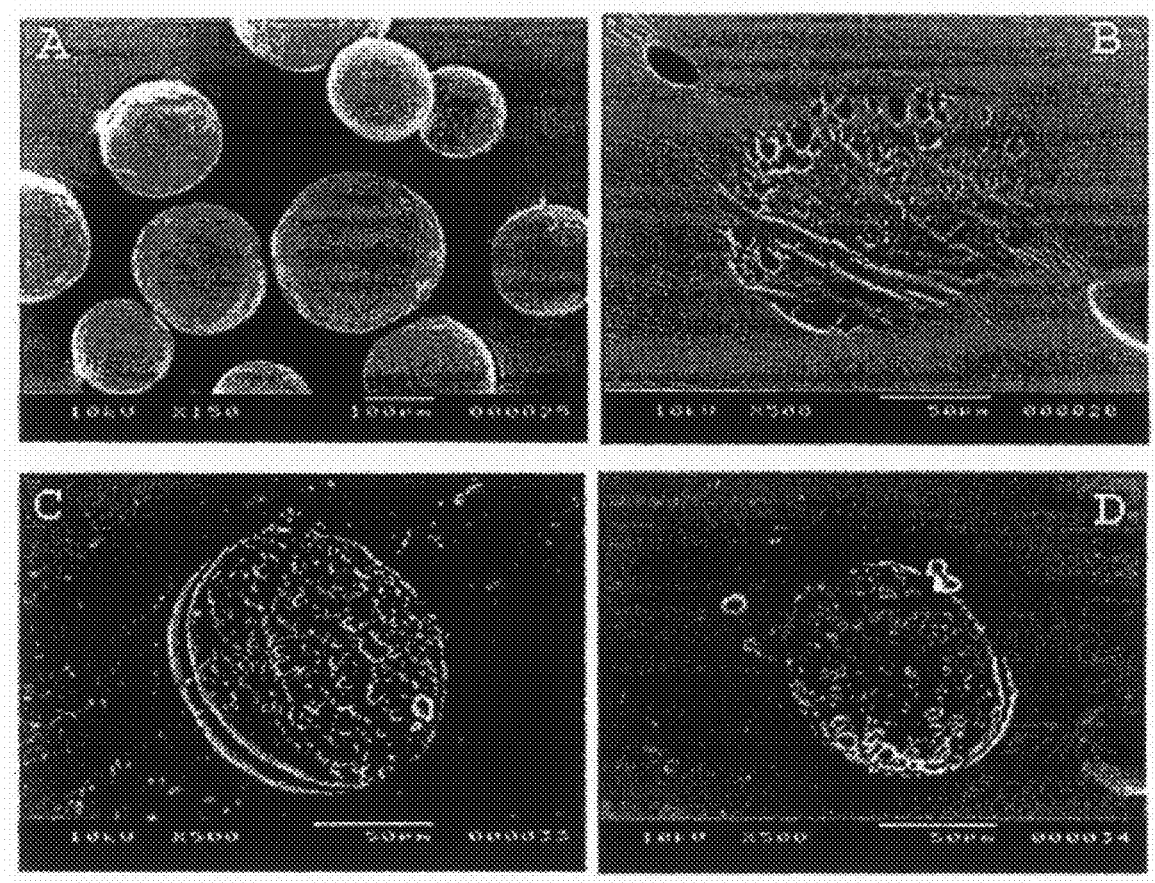
FIG. 9 is a photograph of a scanning electron microscope showing the outer (FIG. 9A) and inner shape (FIGS. 9B to 9D) of a polymeric microsphere containing a drug (risperidone) produced in one embodiment according to the present invention.

The inner and outer shapes of the microspheres produced according to the present invention were observed by using a JSM-5200 scanning electron microscope, and the results are shown in FIGS. 9A to 9D. The outer shape of microspheres is shown in FIG. 9A, in which the microspheres can be seen that they were well dispersed in a spherical form. The inner shapes of the cut microspheres are shown in FIGS. 9B to 9D, in which the shapes were found to be similar, regardless of the loading dose of risperidone and a small size cavity was observed in the matrix. That is, it can be seen that the microspheres produced according to the present invention were well dispersed without cohesion.

Comparative Example

Production of DCM Microsphere by Solvent Evaporation Method

In order to compare the PLGA microsphere produced by the method of the present invention with PLGA microsphere produced by the known solvent evaporation method, the present inventors produced microspheres as follows. PLGA (250 mg) was completely dissolved in 4 ml of dichloromethane, and then progesterone (60, 100, 160, 200, or 250 mg) was added thereto, and dissolved. A dispersion phase consisting of PLGA, progesterone, and dichloromethane was added to 40 ml of 0.5% aqueous solution of polyvinyl alcohol, and emulsified. At this time, a magnetic stirrer was used to produce an emulsion, and the stirring speed of the magnetic bar was maintained at 550 rpm. After stirring for 5 hours, the formed microsphere suspension was passed through a sieve having a size of 425 μm. Then, microspheres were taken by filtration, and dried under vacuum overnight. Consequently, the PLGA microspheres were produced. Hereinbelow, the PLGA microspheres produced by the above described process are referred to as 'DCM microsphere'.

Example 4

PLGA Microsphere Using Methyl Chloroacetate (Hereinbelow, 'MCA Microsphere')

<4-1> Production of MCA Microsphere Using Methyl Chloroacetate

PLGA used in Example <3-1> was used as a polymer for microsphere production. Progesterone was used as a hydrophobic drug to be encapsulated in microspheres. PLGA (250, 300, or 350 mg) was completely dissolved in 4 ml of methyl chloroacetate, and then progesterone (60, 100, 160, 200, or 250 mg) was added thereto to be dissolved. A dispersion phase consisting of PLGA, progesterone, and methyl chloroacetate was added to 40 ml of 0.5% aqueous solution of polyvinyl alcohol, and emulsified. At this time, a magnetic stirrer was used to produce an emulsion, and the stirring speed of magnetic bar was maintained at 550 rpm. After stirring for 3 minutes, 4 ml of ammonia solution (about 28% concentration) was added to the emulsion, and stirred for 10 minutes. Then, 40 ml of water was added thereto, and further stirred for 5 minutes. The formed microsphere suspension was passed through a sieve having a size of 425 μm. Then, microspheres were taken by filtration, and dispersed in 80 ml of 0.1% aqueous solution of polyvinyl alcohol. After 2 hours, the microspheres was filtered and separated, and dried under vacuum overnight. Consequently, the PLGA microspheres were produced. Hereinbelow, the PLGA microspheres produced by the above described process are referred as 'MCA microsphere'.

<4-2> Determination of Encapsulation Efficiency of Progesterone

The median sizes of the microspheres containing progesterone in Example <4-1> ('MCA' microsphere) were precisely measured by using a mastersizer 2000 (Malvern Instruments, Worcestershire, England), and completely dissolved in 4 ml of tetrahydrofuran. 24 ml of methanol was added thereto, and filtered with a nylon filter having a pore size of 0.45 μm. The PLGA precipitate was removed therefrom, and the filtrate was prepared. Some of the filtrate (20 μl) was applied to HPLC, and the drug concentration was determined. The drug encapsulation efficiency (%) was calculated using Equations described in Example <3-4>, and the production rate of microsphere was calculated using the following Equation 4. The results are shown in Table 1.

Production rate=100×weight of recovered microspheres/(amount of PLGA used+amount of progesterone used) [Equation 4]

TABLE 1

Encapsulation efficiency of progesterone in MCA microsphere, production rate and diameter of microsphere

| Composition of microsphere (mg) | | Encapsulation efficiency of progesterone | Production rate of microsphere | Diameter of microsphere |
|---|---|---|---|---|
| PLGA | Progesterone | (%) | (%) | (μm) |
| 250 | 160 | 68.9 ± 1.4 | 76.8 ± 6.4 | 167.2 ± 10.3 |
| 300 | 160 | 67.1 ± 1.3 | 81.3 ± 4.4 | 178.9 ± 19.6 |
| 350 | 160 | 65.9 ± 1.44 | 83.6 ± 5.0 | 181.1 ± 10.6 |

Figure 10:
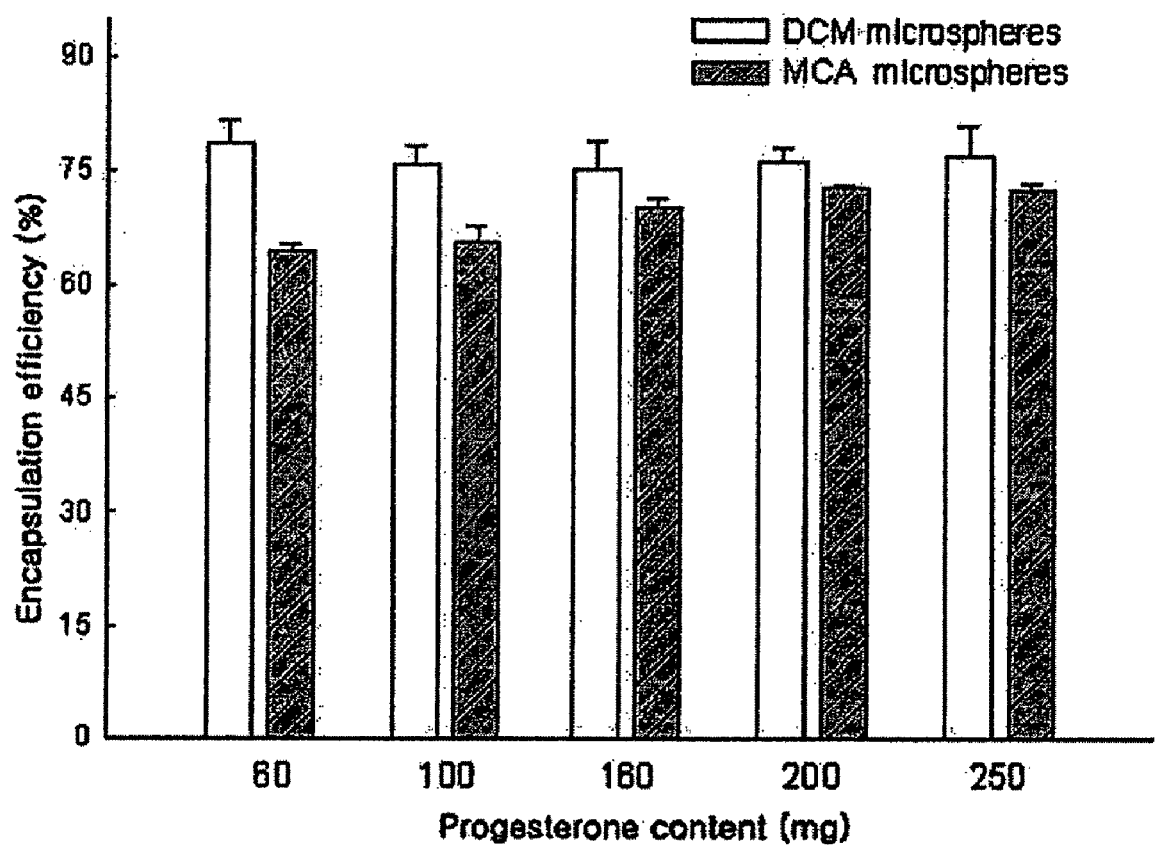
FIG. 10 is a graph comparing the encapsulation efficiency of drug (progesterone) in MCA microsphere produced in one embodiment according to the present invention to that in DCM microsphere.

Meanwhile, encapsulation efficiencies were determined according to the amounts of progesterone, which are used in 'MCA microsphere' that was produced in Example <4-1> (limited to 250 mg of PLGA used) and 'DCM microsphere' that was produced in Comparative Example, and the results are shown in FIG. 10. As shown in FIG. 10, in the MCA microsphere, as the used amounts of progesterone increased, the encapsulation efficiencies gradually increased. In the case where the used amount of progesterone is 250 mg, the encapsulation efficiency reached 72.8±0.3%, and in DCM microsphere, the encapsulation efficiencies were found to be 75.2±3.8% to 78.6±3.1%. Accordingly, as the used amounts of progesterone increased, the encapsulation efficiency of MCA microsphere was found to be similar to that of DCM microsphere.

Therefore, as the used amounts of progesterone increased, the encapsulation efficiency of MCA microspheres that are produced using methyl chloroacetate by ammonolysis was better, thereby being used as good polymeric microspheres loaded with drugs.

<4-3> Thermogravimetric Analysis

Figure 11:
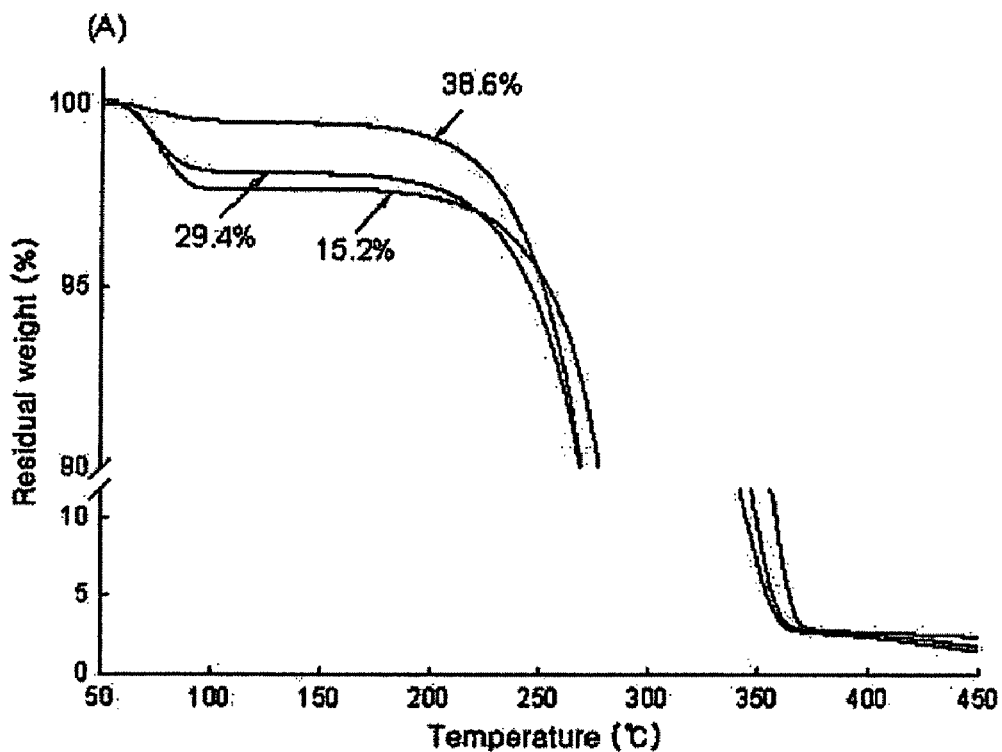
FIG. 11 is thermogravimetric analysis curves of MCA microsphere containing drug (progesterone) (FIG. 11B) produced in one embodiment according to the present invention and DCM microsphere (FIG. 11A)
Figure 11:
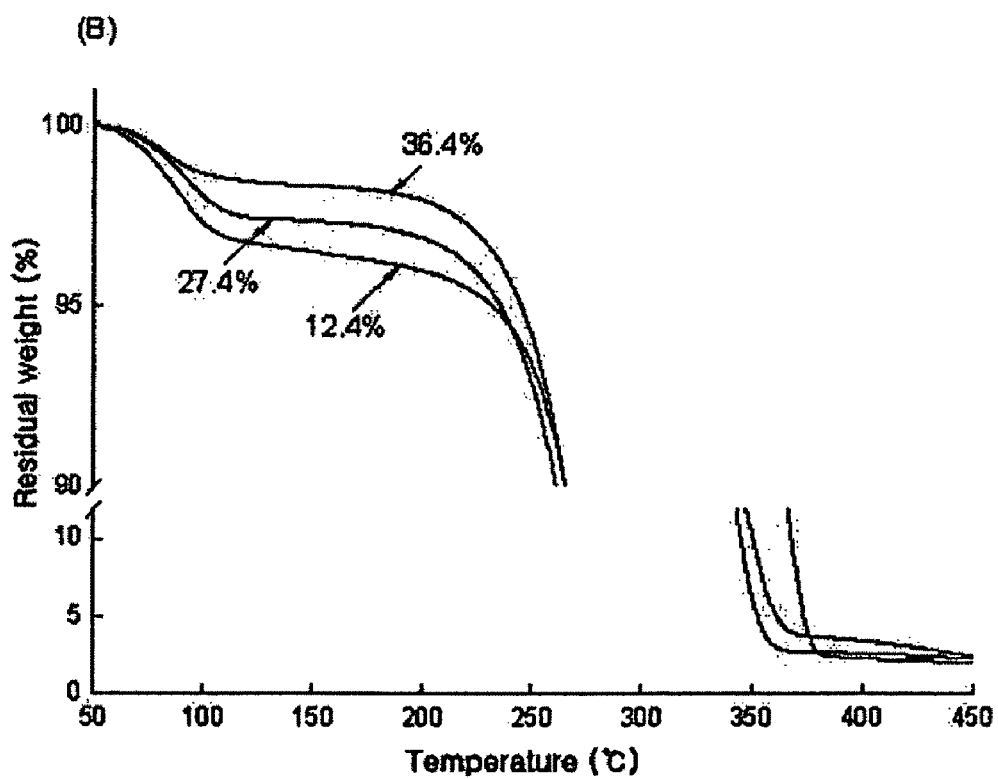

Thermogravimetric analysis of the MCA microspheres loaded with 12.4, 27.4, and 36.4% progesterone that were produced in the same manner as in Example <4-1> and the DCM microspheres with 15.2, 29.4, and 38.6% progesterone that were produced in the same manner as in Comparative Example was performed by using a thermal gravimetric analyzer, TGA 2050 (TA Instruments, US), and the results are shown in FIG. 11. In this connection, nitrogen gas was used, and the change in microsphere weight was measured as the temperature was increased at a rate of 10° C. per minute.

As shown in FIG. 11A, in the DCM microspheres, 0.5 to 2.3% weight loss was found due to the evaporation of dichloromethane at 150° C., which corresponds to the event typically generated during solvent evaporation (Benoit, T. S.; Courteille, F.; Thies, C. Int. J. Pharm. 1986, 29, 95-102). However, as shown in FIG. 11b, in the MCA microspheres, 1.6 to 3.5% weight loss was found, and there was no dramatic weight loss at 129.5° C., which is the boiling point of methyl chloroacetate. The results indicate that the dispersion solvent was effectively removed from the emulsion droplets by ammonolysis.

<4-5> Observation of Microsphere Shape

The surface and inner shapes of the microspheres produced in the same manners as in Example <4-1> and Comparative Example were observed by using a JSM-5200 scanning electron microscope.

Figure 12:
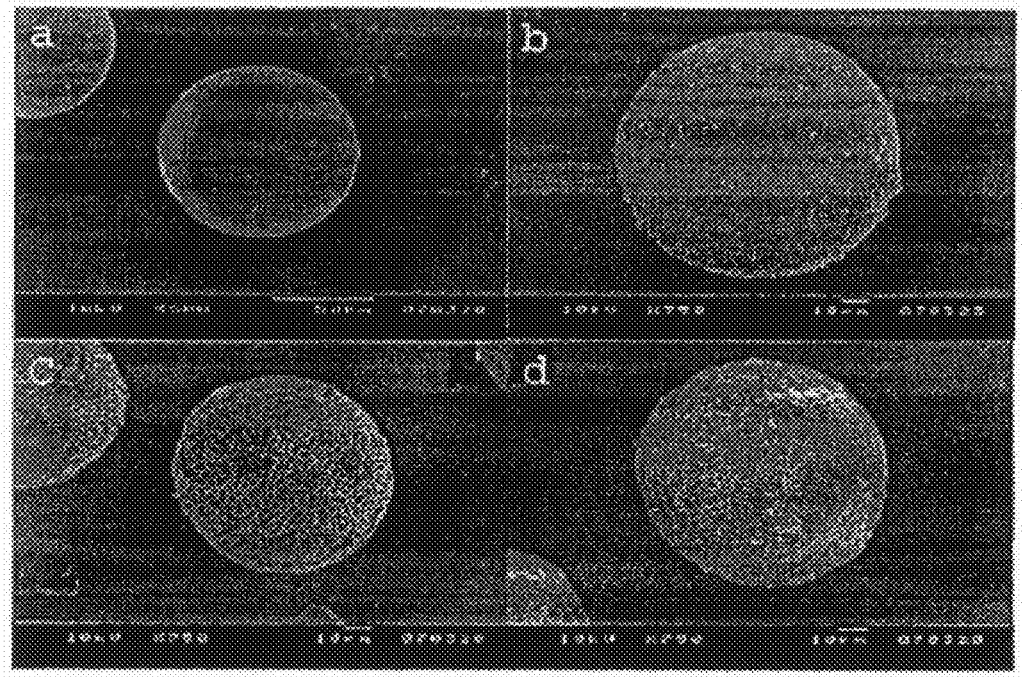
FIG. 12 is a photograph of a scanning electron microscope comparing the surface shape of MCA microsphere containing a drug (progesterone) produced in one embodiment according to the present invention (FIG. 12B) to that of DCM microsphere (FIG. 12A)
Figure 12:
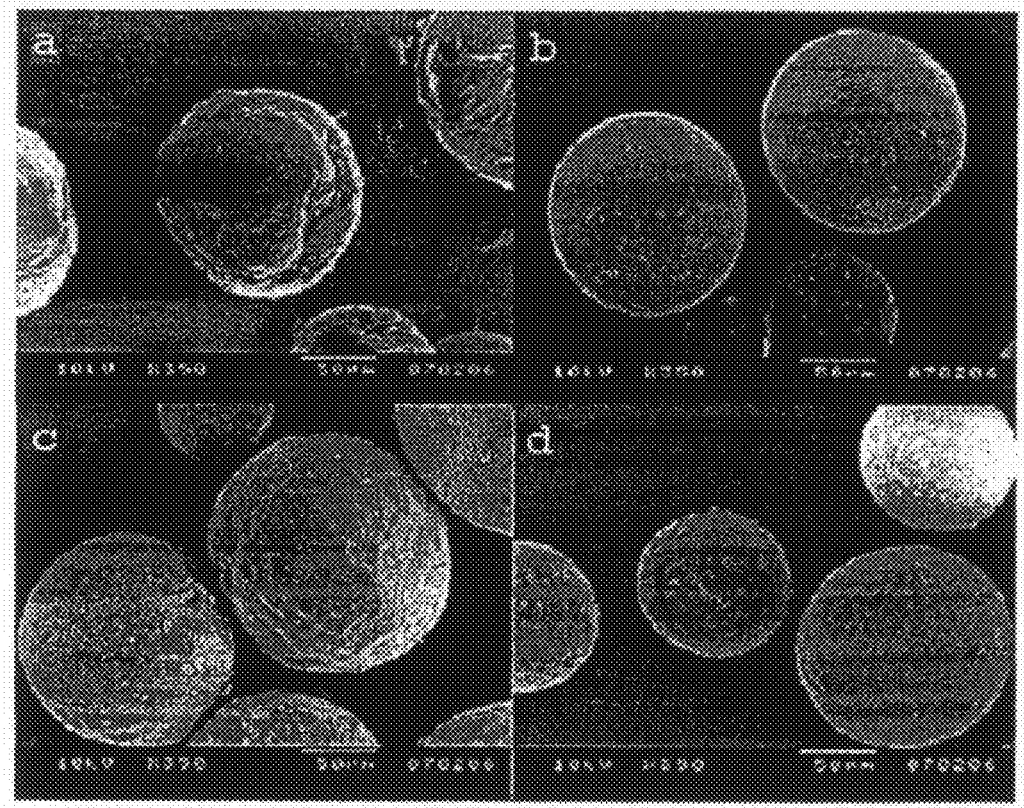

The surface shapes of DCM microspheres, in which the practical loading doses of progesterone are 15.2, 21.7, 29.4, and 38.6% according to Equations 2 in Example <3-4> are illustrated in a, b, c, and d in FIG. 12A, respectively. As shown in FIG. 12A, in the DCM microspheres, as the contents of progesterone increase, progesterone crystals are formed, and the surface of the microspheres are damaged.

Further, the surface shapes of MCA microspheres, in which the practical loading doses of progesterone are 12.4, 18.7, 27.4, and 36.4% are illustrated in a, b, c, and d in FIG. 12B, respectively. As shown in FIG. 12B, as the contents of progesterone increase, no defects occur, the spherical microspheres are formed, and drug crystal formation in DCM microsphere is inhibited.

Figure 13:
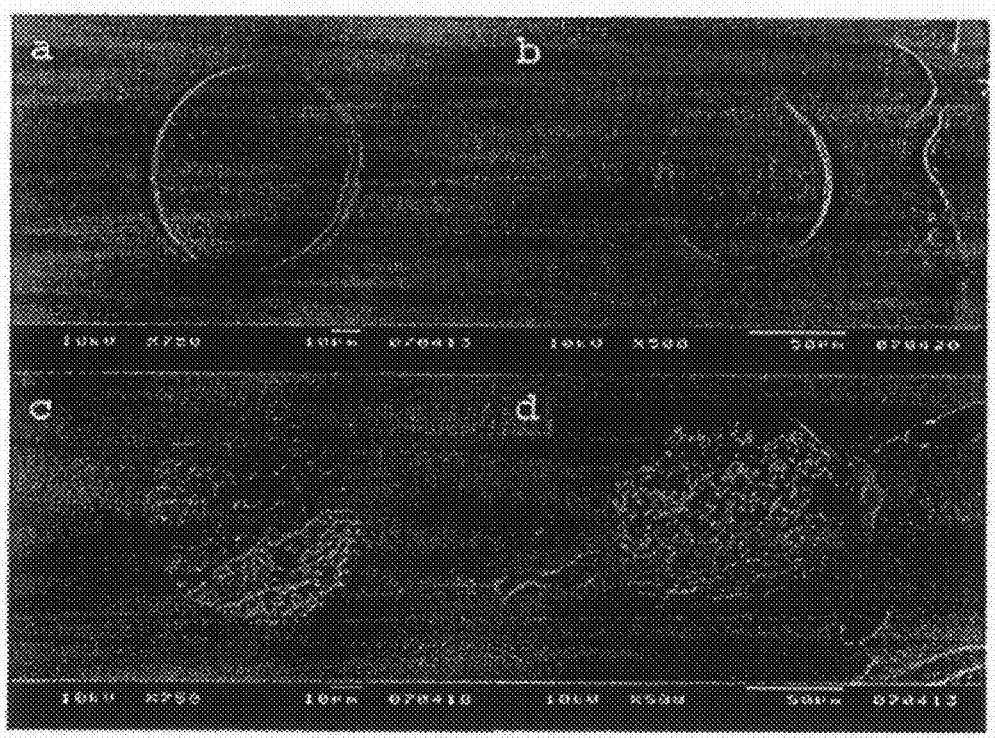
FIG. 13 is a photograph of the scanning electron microscope comparing the inner shape of MCA microsphere containing a drug (progesterone) produced in one embodiment according to the present invention (FIG. 13B) to that of DCM microsphere (FIG. 13A)
Figure 13:
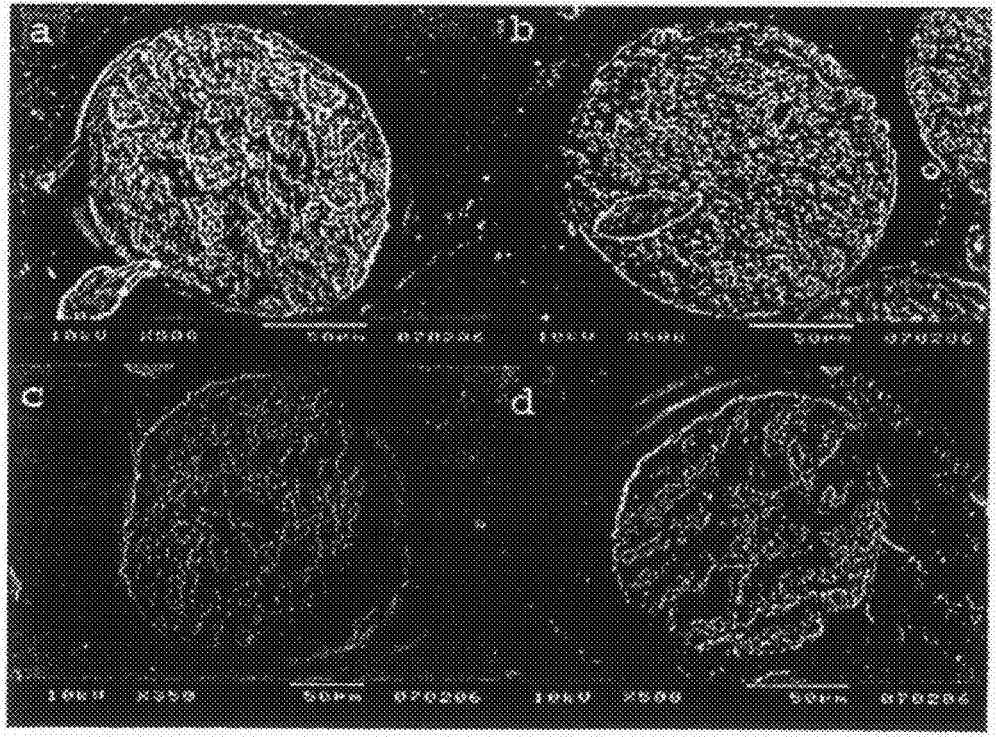

Further, the inner shapes of DCM microspheres, in which the practical loading doses of progesterone are 15.2, 21.7, 29.4, and 38.6% are illustrated in a, b, c, and d in FIG. 13A, respectively. As shown in FIG. 13A, in the DCM microspheres, as the contents of progesterone increase, progesterone crystals are formed to accelerate the phase separation between progesterone and PLGA polymer. Finally, the inner matrix of microsphere was found to be distorted.

Further, the surface shapes of MCA microspheres, in which the practical loading doses of progesterone are 12.4, 18.7, 27.4, and 36.4% are illustrated in a, b, c, and d in FIG. 13B, respectively. As shown in FIG. 13B, a small size of cavity is observed in the matrix. However, the changes according to the content of progesterone were not observed, as compared to the DCM microspheres.

Accordingly, even though a large amount of progesterone is loaded, the surface and inner shapes of MCA microspheres are maintained, thereby being used as good polymeric microspheres loaded with drugs.

Example 5

PLGA Microsphere Using Ethyl Chloroacetate

<5-1> Production of PLGA Microsphere Using Ethyl Chloroacetate

PLGA used in Example <3-1> was used as a polymer for microsphere production. Progesterone was used as a hydrophobic drug to be encapsulated in microspheres. 250 mg of PLGA were completely dissolved in 4 ml of ethyl chloroacetate, and then progesterone (60, 100, 160, 200, or 250 mg) was added thereto to be dissolved. Then, the solution was added to 40 ml of 0.5% aqueous solution of polyvinyl alcohol, and stirred at 550 rpm. After stirring for 3 minutes, 9 ml of ammonia solution (28%) was added to the emulsion, and further stirred for 60 minutes. Then, PLGA microspheres were produced in the same manner as in Example <4-1>.

<5-2> Determination of Encapsulation Efficiency of Progesterone

The median sizes of the microspheres containing progesterone in Example <5-1> were precisely measured by using a mastersizer 2000 (Malvern Instruments, Worcestershire, England), and completely dissolved in 4 ml of tetrahydrofuran. 24 ml of methanol was added thereto, and filtered with a nylon filter having a pore size of 0.45 μm. The PLGA precipitate was removed therefrom, and the filtrate was prepared. Some of the filtrate (20 μl) was applied to HPLC, and the drug concentration was determined. The drug encapsulation efficiency (%) was calculated using Equations described in Example <3-4>, and the results are shown in Table 2.

TABLE 2

| Encapsulation efficiency of progesterone in PLGA microsphere | | |
|---|---|---|
| Composition of microsphere (mg) | | Encapsulation efficiency of |
| PLGA | Progesterone | progesterone (%) |
| 250 | 60 | 87.96 ± 1.22 |
| 250 | 100 | 87.06 ± 1.24 |
| 250 | 160 | 84.77 ± 0.75 |
| 250 | 200 | 85.01 ± 1.27 |
| 250 | 250 | 86.22 ± 1.60 |

As shown in Table 2, it was found that the encapsulation efficiencies of progesterone in PLGA microsphere that are produced by using ethyl chloroacetate by ammonolysis reach 84.77±0.75 to 87.96±1.22, thereby being used as good polymeric microspheres loaded with drugs.

<5-3> Observation of Microsphere Shape

The surface shapes of the PLGA microspheres (FIG. 14B) produced in the same manners as in Example <5-1>, in which the practical loading doses of progesterone are 43.1%, were observed by using a JSM-5200 scanning electron microscope, as compared to the PLGA microspheres containing no progesterone (FIG. 14A).

Figure 14:
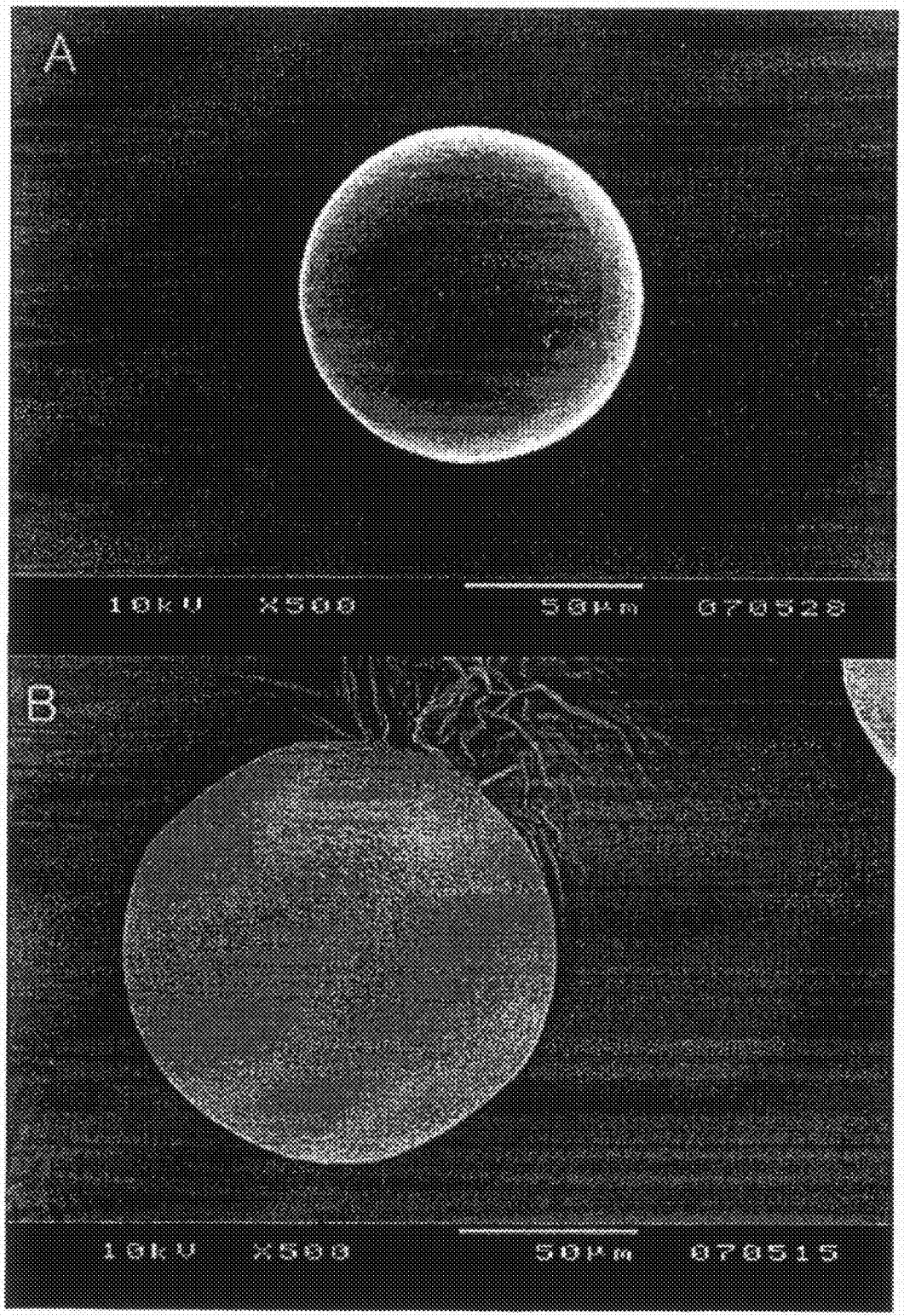
FIG. 14 is a photograph of the scanning electron microscope comparing the surface shape of PLGA microsphere containing a drug (progesterone) produced in one embodiment according to the present invention (FIG. 14B) to that of PLGA microsphere containing no drug (progesterone) (FIG. 14A)

As shown in FIG. 14, it was found that even though progesterone is loaded, the surface shapes of PLGA microspheres are maintained, thereby being used as good polymeric microspheres loaded with drugs.

Example 6

PLGA Microsphere Using Ethyl Fluoroacetate

<6-1> Production of PLGA Microsphere Using Ethyl Fluoroacetate

PLGA used in Example <3-1> was used as a polymer for microsphere production. Progesterone was used as a hydrophobic drug to be encapsulated in microspheres. 250 mg of PLGA were completely dissolved in 4 ml of ethyl fluoroacetate, and then progesterone (60, 100, 160, 200, or 250 mg) was added thereto to be dissolved. Then, PLGA microspheres were produced in the same manner as in Example <5-1>.

<6-2> Determination of Encapsulation Efficiency of Progesterone

The median sizes of the microspheres containing progesterone in Example <6-1> were precisely measured by using a mastersizer 2000 (Malvern Instruments, Worcestershire, England), and completely dissolved in 4 ml of tetrahydrofuran. 24 ml of methanol was added thereto, and filtered with a nylon filter having a pore size of 0.45 μm. The PLGA precipitate was removed therefrom, and the filtrate was prepared. Some of the filtrate (20 μl) was applied to HPLC, and the drug concentration was determined. The drug encapsulation efficiency (%) was calculated using Equations described in Example <3-4>, and the results are shown in Table 3.

TABLE 3

Encapsulation efficiency of progesterone in PLGA microsphere

| Composition of microsphere (mg) | | Encapsulation efficiency of |
|---|---|---|
| PLGA | Progesterone | progesterone (%) |
| 250 | 60 | 81.16 ± 2.40 |
| 250 | 100 | 81.42 ± 1.90 |
| 250 | 160 | 82.82 ± 1.36 |
| 250 | 200 | 84.01 ± 2.31 |
| 250 | 250 | 84.56 ± 2.02 |

As shown in Table 3, it was found that the encapsulation efficiencies of progesterone in PLGA microsphere that are produced by using ethyl fluoroacetate by ammonolysis reach 81.16±2.40 to 84.56±2.02, thereby being used as good polymeric microspheres loaded with drugs.

<6-3> Observation of Microsphere Shape

The surface shapes of the PLGA microspheres (FIG. 15B) produced in the same manners as in Example <6-1>, in which the practical loading doses of progesterone are 42.3%, were observed by using a JSM-5200 scanning electron microscope, as compared to the PLGA microspheres containing no progesterone (FIG. 15A).

Figure 15:
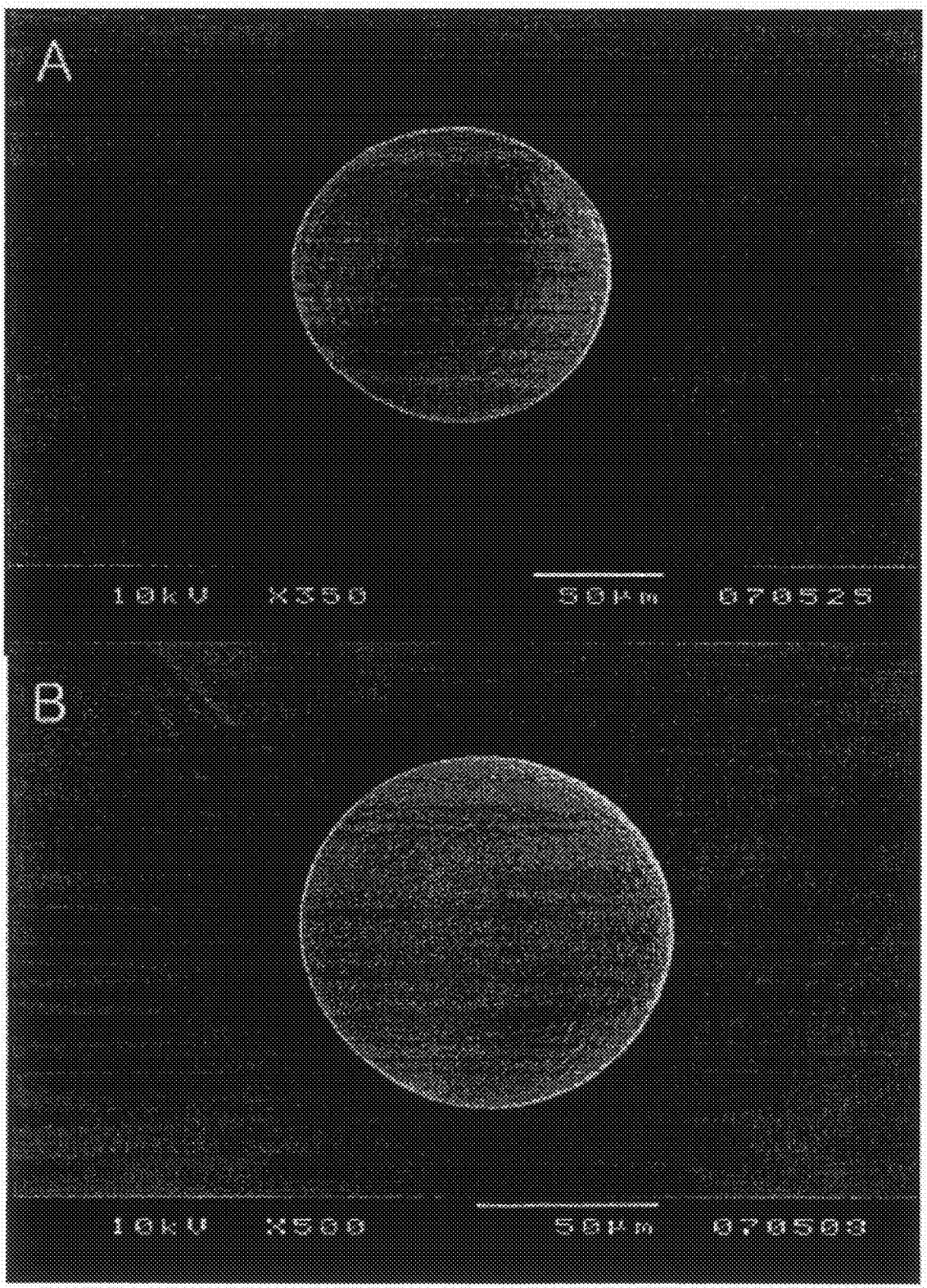
FIG. 15 is a photograph of the scanning electron microscope comparing the surface shape of PLGA microsphere containing a drug (progesterone) produced in one embodiment according to the present invention (FIG. 15B) to that of PLGA microsphere containing no drug (progesterone) (FIG. 15A).

As shown in FIG. 15, it was found that even though progesterone is loaded, the surface shapes of PLGA microspheres are maintained, thereby being used as good polymeric microspheres loaded with drugs.

The invention claimed is:

1. A method for producing polymeric microspheres loaded with drugs, the method comprising the steps of:
   a) adding a dispersion phase containing a high molecular compound, a drug, and a water-insoluble organic solvent to a dispersion solvent to produce an O/W (oil-in-water) type or O/O (oil-in-oil) type emulsion, or adding a W/O (water-in-oil) type emulsion, which is prepared by emulsifying an aqueous solution, in which a drug is dissolved, in a water-insoluble organic solvent, in which the high molecular compound is dissolved, to the dispersion solvent to produce a W/O/W (water-in-oil-in-water) type emulsion; and
   b) adding an ammonia solution to the emulsion produced in step a) to convert the water-insoluble organic solvent into water-soluble solvents
   wherein the addition of ammonia solution results in ammonolysis of water-insoluble organic solvent in the emulsion to convert the water-insoluble organic solvent into water-soluble solvents, and wherein the water-soluble solvents dissolve in aqueous solution to harden a droplet of the emulsion into the polymeric microsphere.

2. The method for producing polymeric microspheres loaded with drugs according to claim 1, wherein the dispersion solvent of step a) is an aqueous dispersion solvent such as an aqueous solution of polyvinyl alcohol or co-solvent thereof, or a nonaqueous dispersion solvent selected from the group consisting of a span containing silicone oil, vegetable oil, toluene, and xylene.

3. The method for producing polymeric microspheres loaded with drugs according to claim 1, wherein the water-insoluble organic solvent of step a) is a co-solvent that is mixed with a water-insoluble organic solvent and at least one of the other organic solvents.

4. The method for producing polymeric microspheres loaded with drugs according to claim 1, wherein the water-insoluble organic solvent has any one backbone selected from the group consisting of carboxylic esters, carboxylic amides, anhydrides, phosphoric esters, and phosphoric anhydrides.

5. The method for producing polymeric microspheres loaded with drugs according to claim 1, wherein the water-insoluble organic solvent is selected from the group consisting of methyl dichloroacetate, methyl chloroacetate, ethyl chloroacetate, ethyl dichloroacetate, methyl fluoroacetate, methyl difluoroacetate, ethyl fluoroacetate, ethyl difluoroacetate, ethyl acetate, methyl acetate, methyl formate, ethyl formate, isopropyl formate, and propyl formate.

6. The method for producing polymeric microspheres loaded with drugs according to claim 5, wherein the water-insoluble organic solvent is selected from the group consisting of methyl dichloroacetate, methyl chloroacetate, ethyl chloroacetate, and ethyl fluoroacetate.

7. The method for producing polymeric microspheres loaded with drugs according to claim 1, wherein the high molecular compound of the step a) is selected from the group consisting of polylactic acid, polylactide, polylactic-co-glycolic acid, polylactide-co-glycolide (PLGA), polyphosphazene, polyiminocarbonate, polyphosphoester, polyanhydride, polyorthoester, a copolymer of lactic acid and caprolactone, polycaprolactone, polyhydroxyvalerate, polyhydroxybutyrate, polyamino acid, a copolymer of lactic acid and amino acid, and a mixture thereof.

8. The method for producing polymeric microspheres loaded with drugs according to claim 1, wherein the high molecular compound of the step a) is mixed in an amount of 1 to 500 parts by weight, based on 1 part by weight of the drug.

9. The method for producing polymeric microspheres loaded with drugs according to claim 1, wherein the concentration of the high molecular compound contained in the emulsion of step a) is 3 to 30% (w/v).

10. The method for producing polymeric microspheres loaded with drugs according to claim 1, wherein a volume ratio of the dispersion phase or W/O (water-in-oil) type emulsion, and the dispersion solvent of step a) is 1:1 to 100.

11. The method for producing polymeric microspheres loaded with drugs according to claim 1, wherein a volume ratio of the aqueous solution, in which the drug is dissolved, and the water-insoluble organic solvent, in which the high molecular compound is dissolved, of step a) is 1:1 to 50.

12. The method for producing polymeric microspheres loaded with drugs according to claim 1, wherein the ammonia solution of step b) contains higher molarity of ammonia than that of water-insoluble organic solvent.

* * * * *